US005238936A

United States Patent [19]

Regnier et al.

[11] Patent Number: 5,238,936

[45] Date of Patent: Aug. 24, 1993

[54] TRISUBSTITUTED TRIAZINES

[75] Inventors: Gilbert Regnier, Chatenay Malabry; Alain Dhainaut, Chatou; Ghanem Atassi, Saint Cloud; Alain Pierre, Marly le Roi; Stéphane Leonce, Versailles, all of France

[73] Assignee: Adir et Compagnie, Courbevoie, France

[21] Appl. No.: 847,916

[22] Filed: Mar. 6, 1992

[30] Foreign Application Priority Data

Mar. 7, 1991 [FR] France ............................... 91 02710

[51] Int. Cl.[5] .................. C07D 401/04; C07D 401/06; C07D 401/12; C07D 403/04; C07D 403/06; C07D 405/14; C07D 403/12; A61K 31/53

[52] U.S. Cl. .................................... 514/245; 514/211; 514/212; 514/217; 514/216; 514/220; 514/219; 514/224.5; 514/225.8; 514/229.5; 514/229.8; 544/43; 544/104; 544/37; 544/102; 544/207; 544/212; 544/198; 540/575; 540/598; 540/460; 540/461; 540/468; 540/469; 540/471; 540/479; 540/488; 540/489; 540/495; 540/522; 540/548; 540/549; 540/547; 540/545; 540/557; 540/590

[58] Field of Search ............... 544/209, 198, 207, 212, 544/198, 102, 43; 514/245, 211, 216, 224.5, 229.8; 540/575, 488, 522, 547, 590, 468, 479

[56] References Cited

PUBLICATIONS

Hayashi et al., Chemical Abstracts, vol. 111, entry 25008g (1988).

*Primary Examiner*—John M. Ford
*Attorney, Agent, or Firm*—Gordon W. Hueschen

[57] ABSTRACT

The compounds are trisubstituted triazines and pyrimidines useful for the suppressing the resistance of tumour cells to anti-cancer agents and for suppressing the resistance of parasites to anti-parasitic agents.

A compound disclosed is 2,4-diallylamino-6-{4-[(10,11-dihydro-5H-dibenzo[a,d]cyclohepten-5-yl) methylamino]piperidin-1-yl}-1,3,5-triazine.

10 Claims, No Drawings

TRISUBSTITUTED TRIAZINES

The present invention relates to trisubstituted triazines and pyrimidines, a process for their preparation, and pharmaceutical compositions comprising them.

It relates especially to trisubstituted triazines and pyrimidines of formula I:

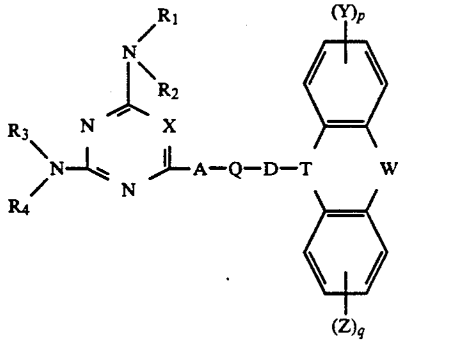

(I)

wherein :

$R_1$, $R_2$, $R_3$ and $R_4$ are the same or different and each represents a hydrogen atom, a cycloalkyl radical having from 3 to 6 carbon atoms or a straight-chain or branched alkyl radical having from 1 to 6 carbon atoms that optionally contains a double or a triple bond and is optionally substituted by a halogen atom, by one or more hydroxy radicals, or by an amino radical

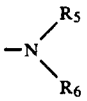

wherein $R_5$ and $R_6$ are the same or different and each represents a hydrogen atom or an alkyl radical having from 1 to 5 carbon atoms, or $R_5$ and $R_6$, together with the nitrogen atom to which they are bonded, form a pentagonal, hexagonal or heptagonal heterocycle optionally containing an oxygen or sulphur atom;

X represents a nitrogen atom or the group CH;

A represents a single bond, a straight-chain or branched hydrocarbon radical having from 1 to 3 carbon atoms, or a group —NH—A'— wherein A' represents a hydrocarbon chain having from 2 to 6 carbon atoms that optionally contains an oxygen or sulphur atom and is optionally substituted by a hydroxy radical;

Q represents a heterocyclic radical of formula:

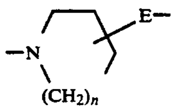 or 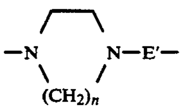

wherein:

n represents an integer of from 1 to 3,

E represents an oxygen or sulphur atom or an —NR— or —$CH_2$NR— radical, R representing a hydrogen atom or an alkyl or alkenyl radical each having up to 5 carbon atoms, and E' represents a single bond or an —NR— radical as defined above;

D represents a single bond or a straight-chain or branched hydrocarbon radical having up to 6 carbon atoms;

T represents:

a CR' radical wherein R' represents a hydrogen atom or an alkyl radical having from 1 to 5 carbon atoms, a 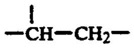 racial or a nitrogen atom;

W represents:

a single bond, a CHR" radical wherein R" represents a hydrogen atom or an alkyl radical having from 1 to 5 carbon atoms, a di- or tri-methylene radical [$(CH_2)_2$ and $(CH_2)_3$], a —CH=CH— radical, an oxygen or sulphur atom, an NR''' radical wherein R''' represents a hydrogen atom or an alkyl radical having from 1 to 5 carbon atoms, a radical of formula:

CO, $SO_2$, —$CH_2$—O—, —$CH_2$—S—, —$CH_2$—$SO_2$—,

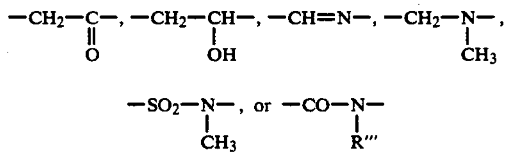

wherein R''' is as defined hereinbefore; and furthermore, when T and W represent CR' and CHR" respectively and R' and R" are other than H, R' and R" may together represent a polymethylene bridge having 2 or 3 carbon atoms;

Y and Z are the same or different and each represents a hydrogen atom, a halogen atom, a trifluoromethyl radical, or an alkyl or alkoxy radical each having from 1 to 3 carbon atoms; and p and q are the same or different and are each 1 or 2;

and, when formula I contains one or more chiral carbon atoms, the corresponding enantiomers or diastereoisomers.

The prior art is illustrated especially by French Patent No. 2 524 467, which relates to trisubstituted triazines and pyrimidines of formula:

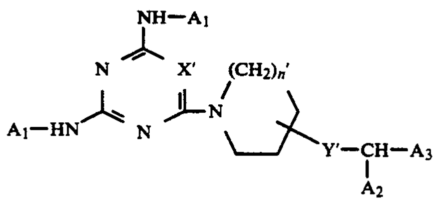

wherein:

$A_1$ represents a $C_3$–$C_5$alkenyl radical optionally substituted by one or more OH radicals;

X' represents CH or N;

n' represents zero, one or two;

Y' represents O or N—R'$_1$ [R'$_1$ representing hydrogen, ($C_1$-$C_5$)-alkyl or -hydroxyalkyl, ($C_2$-$C_5$)-alkenyl, or ($C_3$-$C_7$)-cycloalkyl or -cycloalkenyl];

$A_2$ represents hydrogen, ($C_1$-$C_5$)-alkyl, ($C_5$-$C_7$)-cycloalkyl or optionally substituted phenyl, and $A_3$ represents especially ($C_1$-$C_5$)-alkyl, ($C_2$-$C_5$)-alkenyl, phenyl, naphthyl, benzofuranyl, benzothienyl benzodioxolyl, benzodioxanyl, benzodioxinyl, Δ3-chromenyl, thiochromenyl or chromanyl;

which triazines and pyrimidines promote the uptake of oxygen and may thus be used in the treatment of cerebral decline.

Substantial structural modifications have resulted in the compounds of formula I of the present invention, which have a particularly valuable pharmacological and therapeutic activity that is totally different from that of close prior art compounds, as demonstrated by the pharmacological study described hereinafter.

The present invention also relates to a process for the preparation of compounds of formula I which is characterised in that either a compound of formula II:

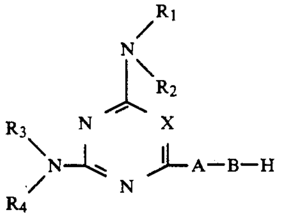

(II)

wherein $R_1$, $R_2$, $R_3$, $R_4$, X, A and B are as defined hereinbefore, is condensed with a compound of formula III:

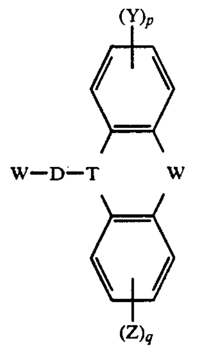

(III)

wherein D, T, W, Y, Z, p and q are as defined hereinbefore and W represents a halogen atom, such as, for example, a chlorine or bromine atom, or a tosyloxy radical;

or a halogenated compound of formula IV:

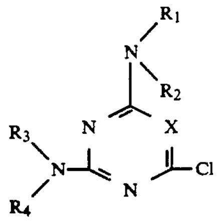

(IV)

wherein $R_1$, $R_2$, $R_3$, $R_4$ and X are as defined hereinbefore, is condensed with a compound of formula V:

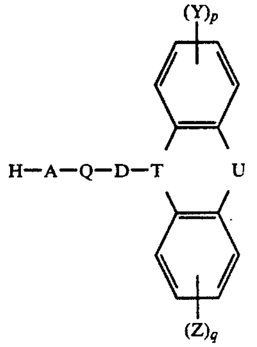

(V)

wherein A, Q, D, T, U, Y, Z, p and q are as defined hereinbefore.

The condensation of compounds II and III is preferably carried out in a solvent selected from alcohols containing 4 or 5 carbon atoms, dimethylformamide, dimethyl acetamide, acetonitrile, tetrahydrofuran, methyl ethyl ketone, and aromatic hydrocarbons having a high boiling point.

It is advantageous to carry out the condensation at a temperature of from 80° to 120° C. in the presence of an acceptor for the acid formed during the course of the reaction. The acceptor may be selected from alkaline carbonates, such as potassium carbonate, triethylamine and an excess of the compound II used for the condensation.

On the other hand, when Q represents the radical

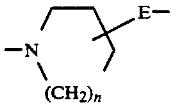

wherein n has the meaning given hereinbefore and E represents only an oxygen or sulphur atom [which means that Q represents:

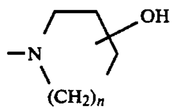 or 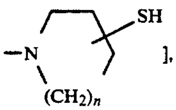 ], it is expedient to use sodium hydride to form the sodium derivative of compound II beforehand.

The condensation of compounds IV and V is carried out particularly expediently in a solvent selected from alcohols containing 4 or 5 carbon atoms, such as butanol or pentanol, and aliphatic amides, such as dimethylformamide or dimethyl acetamide. It is recommended that the condensation be carried out at a temperature of from 120° to 150° C. in the presence of an acceptor for the hydracid formed during the course of the reaction.

The acceptor may be selected from alkaline carbonates, such as potassium carbonate, triethylamine and an excess of the compound V used for the condensation.

On the other hand, when A represents a single bond and Q represents the radical

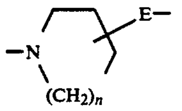

wherein n has the meaning given hereinbefore and E represents only an oxygen or sulphur atom (which means that HAQ— represents:

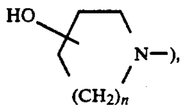

it is expedient to use sodium hydride to form the sodium derivative of compound V beforehand.

The present invention also relates to a process for the preparation of compounds I wherein B represents the radical

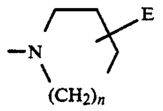

wherein n has the meaning given hereinbefore and E represents an —NR radical, that is to say, more specifically, the compounds of formula I':

(I')

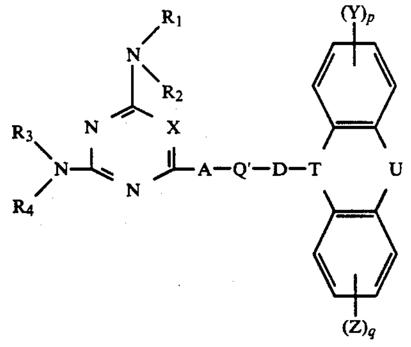

wherein $R_1$, $R_2$, $R_3$, $R_4$, X, A, D, T, U, Y, Z, p and q are as defined hereinbefore, and Q' represents the radical:

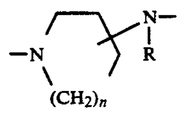

wherein n and R are as defined hereinbefore, characterised in that a compound of formula VI:

(VI)

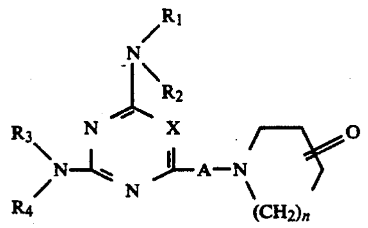

wherein $R_1$, $R_2$, $R_3$, $R_4$, X, A and n are as defined hereinbefore, is condensed with a compound of formula VII:

(VII)

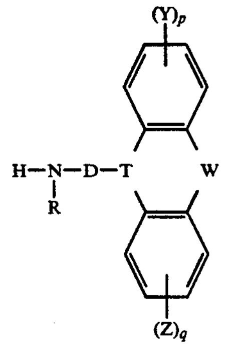

wherein R, D, T, U, Y, Z, p and q are as defined hereinbefore.

It is especially advantageous to carry out the reaction in the presence of sodium cyanoborohydride, in an appropriate solvent, such as a low-molecular-weight alcohol, for example methanol, ethanol or propanol, or tetrahydrofuran, at a temperature of from 15° to 20° C. and at a pH of approximately 6.

The starting materials used in the above-described processes are either known compounds, or compounds prepared from known substances according to processes described for the preparation of analogous compounds as indicated in the following Examples.

The compounds of formula I may be converted into addition salts with acids, which salts, as such, form part of the invention. There may be mentioned as acids that can be used for the formation of those salts, for example, in the mineral series, hydrochloric, hydrobromic, sulphuric and phosphoric acid and, in the organic series. acetic, propionic, maleic, fumaric, tartaric, nitric, oxalic, benzoic, methanesulphonic and isethionic acid.

Moreover, when formula I contains one or more chiral carbon atoms, the compounds (I) may be in the form of enantiomers or diastereoisomers which, as such, also form part of the invention.

The new compounds (I) can be purified by physical methods, such as crystallisation of the bases or salts, chromatographic methods (especially flash chromatography on silica 35-70μ, using $CH_2Cl_2$/methanol or ethyl acetate as the elution system) or chemical methods, such as the formation of addition salts with acids and decomposition of those salts using alkaline agents.

The compounds of formula I and their physiologically tolerable addition salts possess valuable pharmacological and therapeutic properties that enable them to be used to suppress the resistance of tumour cells to anti-cancer agents and to suppress the resistance of parasites to anti-parasitic agents.

The present invention also relates to pharmaceutical compositions comprising as active ingredient a compound of formula I or a physiologically tolerable salt thereof, mixed with or in association with an appropriate pharmaceutical excipient.

The so-obtained pharmaceutical compositions are generally presented in dosage form. They may, for example, be in the form of tablets, dragees, capsules, suppositories or injectable or drinkable solutions, and may be administered by the oral, rectal or parenteral route.

The dosage used may vary, especially in accordance with the age and weight of the patient, the route of administration, the nature of the disorder and associated treatments, and is lower than or equal to 1 g per administration.

The following Examples illustrate the invention. The melting points are determined using a capillary tube (cap) or a Kofler hot plate (K).

EXAMPLE 1

2,4-Diallylamino-6-{4-(10,11-dihydro-5H-dibenzo[a,d-]cyclohepten-5-yl)piperazin-1-yl}-1,3,5-triazine

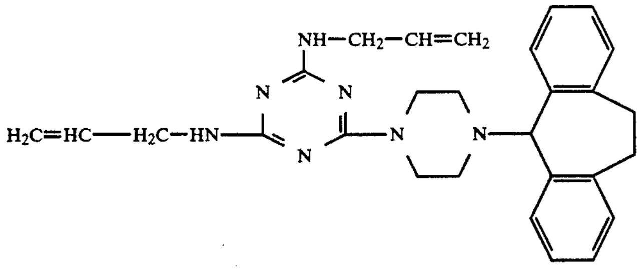

A solution of 13,8 of 2,4-diallylamino-6-(piperazin-1-yl)-1,3,5-triazine [of which the hydrochloride melts (K) at 259°-263° C.] and 12.6 g of 5-chloro-10,11-dihydro-5H-dibenzo[a,d]cycloheptene [melting (K) at 110° C.] in 200 ml of toluene, 20 ml of dimethylformamide and 5.56 g of triethylamine are heated at reflux for 8 hours. When the reaction is complete, the solution is treated with 50 ml of water, and the toluene layer is decanted off. This operation is carried out a further two times. The toluene phases are combined and the toluene is evaporated. The oily residue (26 g) is dissolved at the boil in 150 ml of ethanol. The product crystallises. 10 g of 2,4-diallylamino-6-{4-(10,11-dihydro-5H-dibenzo[a,d]cyclohepten-5-yl)piperazin-1-yl}-1,3,5-triazine crystals, m.p. (K): 192° C., are isolated.

EXAMPLE 2

2,4-Diallylamino-6-{2-[4-(10,11-dihydro-5H-dibenzo[a,d]cyclohepten-5-yl)piperazin-1-yl]ethylamino}-1,3,5-triazine

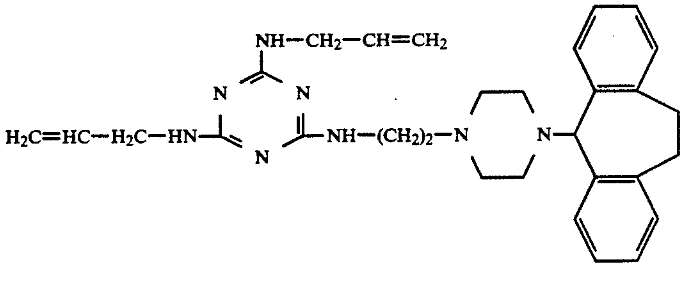

A solution of 3.2 g of 2,4-diallylamino-6-chloro-1,3,5-triazine, melting (K) at 204° C., and 4.5 g of 1-aminoethyl-4-(10,11-dihydro-5H-dibenzo[a,d]cyclohepten-5-yl)-piperazine, melting (cap) at 70°-71° C., in 100 ml of butanol is heated at reflux for 12 hours in the presence of 1.9 g of potassium carbonate and 0.1 g of potassium iodide.

When the reaction is complete, the salt is filtered off, the solvent is evaporated and the residue is taken up in ether, washed with water and dried over $MgSO_4$. After evaporation of the ether, the oily residue is chromatographed on 120 g of silica, using the system $CH_2Cl_2/CH_3OH$ (92/8) as eluant. After evaporation of the eluate, the recovered base is converted into the difumarate in ethanol to yield, ultimately, 7.7 g of 2,4-diallylamino-6-{2-[4-(10,11-dihydro-5H-dibenzo[a,d-]cyclohepten-5-yl)piperazin-1-yl]ethylamino}-1,3,5-triazine difumarate crystals melting (cap) at 123°-128° C. The aminoethylpiperazine starting material was prepared by reducing the corresponding cyanomethyl compound, [m.p. (cap): 112°-113° C.] with $H_2/Ni$, in ethanol, in the presence of $NH_3$.

EXAMPLE 3

2,4-Diallylamino-6-{4-[(10,11-dihydro-5H-dibenzo[a,d-]cyclohepten-5-yl)methylamino]piperidin-1-yl}-1,3,5-triazine

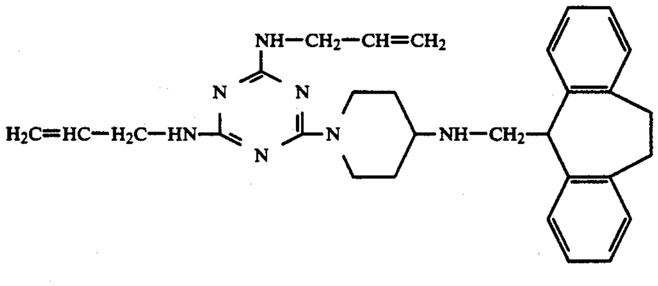

A solution of sodium methoxide, prepared extemporaneously from 1.55 g of sodium, is added at 10° C. to a solution of 20.5 g of 5-aminomethyl-10,11-dihydro-5H-dibenzo[a,d]cycloheptene hydrochloride melting (cap) at 270°-280° C. When the solution is homogeneous, 16.2 g of 1-(4,6-diallylamino-1,3,5-triazin-2-yl)-piperid-4-one hydrochloride, melting (cap) at 219°-222° C., and then 5 g of sodium cyanoborohydride are added, the temperature being held constant at 10° C. The pH of the solution is adjusted to 6 by the addition of methanolic hydrogen chloride and the solution is stirred for 24 hours at room temperature in the presence of a 3Å molecular sieve. When the reaction is complete, the insoluble salt is filtered off and the filtrate is concentrated under reduced pressure.

The residue is then taken up in 150 ml of $CH_2Cl_2$, is washed twice with 100 ml of a 10% $NaHCO_3$ solution each time, and is then washed with water and finally dried over $Na_2SO_4$.

After evaporating off the solvent, the resulting oil is chromatographed on 1 kg of silica (35-70$\mu$) using the eluant system $CH_2Cl_2/CH_3OH$ (95/5). After evaporation of the eluate, the product is recrystallised from ether, yielding 17.5 g of 2,4-diallylamino-6-{4-[(10,11-dihydro-5H-dibenzo[a,d]cyclohepten-5-yl)methylamino]piperidin-1-yl}-1,3,5-triazine in the form of white crystals melting (cap) at 131°-134° C.

The 1-(4,6-diallylamino-1,3,5-triazin-2-yl)-piperid-4-one used as starting material was prepared by acid hydrolysis of the corresponding diethylacetal, which was itself prepared by condensing 4,6-diallylamino-2-chloro-1,3,5-triazine, melting (cap) at 206° C., with 4,4-diethoxypiperidine in butanol under reflux.

The 2,4-diallylamino-6-{4-[(10,11-dihydro-5H-dibenzo[a,d]cyclohepten-5-yl)methylamino]piperidin-1-yl}-1,3,5-triazine was also prepared in accordance with the method described in Example 1.

EXAMPLES 4 TO 32

The following compounds were prepared using one or more of the methods of preparation described in Examples 1 to 3:

4. 2,4-diallylamino-6-[4-(10,11-dihydro-5H-dibenzo[a,d]cyclohepten-5-ylamino)piperidin-1-yl]-1,3,5-triazine, m.p. (cap) of the corresponding fumarate : 187°-190° C., in accordance with Example 1 and Example 3.

5. 2-allylamino-4-propylamino-6-{4-[(10,11-dihydro-5H-dibenzo[a,d]cyclohepten-5-yl)methylamino]piperidin-1-yl}-1,3,5-triazine, m.p. (cap): 118°-121° C., in accordance with Example 1 and Example 3.

6. 2,4-diallylamino-6-{3-[4-(10,11-dihydro-5H-dibenzo[a,d]cyclohepten-5-yl)piperazin-1-yl]-2-hydroxypropylamino}-1,3,5-triazine, amorphous product, in accordance with Example 2.

7. 2,4-diallylamino-6-{[1-(10,11-dihydro-5H-dibenzo[a,d]cyclohepten-5-yl)piperidin-4-yl]methylamino}-1,3,5-triazine, amorphous product, in accordance with Example 2.

8. 2,4-diallylamino-6-{[1-[(10,11-dibenzo[a,d]cyclohepten-5-yl)methyl]piperidin-4-yl]methylamino}-1,3,5-triazine, amorphous product, in accordance with Example 2.

9. 2,4-diallylamino-6-[4-(xanthen-9-ylmethylamino)-piperidin-1-yl]-1,3,5-triazine, m.p. (cap): 70°-77° C., in accordance with Example 3.

10. 2,4-diallylamino-6-{4-[(9,10-dihydro-9,10-ethanoanthracen- 9-yl)methylamino]piperidin-1-yl}-1,3,5-triazine, m.p. (cap): 148°-150° C., in accordance with Example 3.

11. 2,4-diallylamino-6-{4-[(5H-dibenzo[a,d]cyclohepten-5-yl)methylamino]piperidin-1-yl}-1,3,5-triazine, m.p. (cap) of the corresponding difumarate : 203°-205° C., in accordance with Example 3.

12. 2,4-diallylamino-6-{2-[4-(10,11-dihydro-5H-dibenzo[a,d]cyclohepten-5-ylamino)piperidin-1-yl]ethylamino}-1,3,5-triazine, m.p. (cap) of the corresponding difumarate: 128°-131° C., in accordance with Example 3.

13. 2,4-diallylamino-6-{4-[(fluoren-9-yl)methylamino]piperidin-1-yl}-1,3,5-triazine, m.p. (cap) of the corresponding difumarate: 139°-144° C., in accordance with Example 3.

14. 2,4-dimethylamino-6-{4-[(10,11-dihydro-5H-dibenzo[a,d]cyclohepten-5-yl)methylamino]piperidin-1-yl}-1,3,5-triazine, m.p. (cap) of the corresponding fumarate: 234° C., in accordance with Example 3.

15. 2,4-diallylamino-6-(2-[4-(10,11-dihydro-5H-dibenzo-[a,d]cyclohepten-5-ylmethylamino)piperidin-1-yl]ethylamino}-1,3,5-triazine, m.p. (cap) of the corresponding difumarate: 212° C., in accordance with Example 3.

16. 2,4-diallylamino-6-{3-[4-(10,11-dihydro-5H-dibenzo[a,d]cyclohepten-5-ylamino)piperidin-1-yl]-2-hydroxypropylamino}-1,3,5-triazine, m.p. (cap) of the corresponding difumarate: 148°-151° C., in accordance with Example 3.

17. 2,4-diallylamino-6-{3-[4-(10,11-dihydro-5H-dibenzo[ a,d]cyclohepten-5-ylmethylamino)piperidin-1-yl]-2-hydroxypropylamino}-1,3,5-triazine, m.p. (cap) of the corresponding difumarate: 170°-173° C., in accordance with Example 3.

18. 2-allylamino-4-amino-6-{4-[(10,11-dihydro-5H-dibenzo[a,d]cyclohepten-5-yl)methylamino]piperidin-1- yl}-1,3,5-triazine, m.p. (cap) of the corresponding dimaleate: 153°-155° C., in accordance with Example 3.

19. 2,4-diallylamino-6-{4-[((R,S)-6,11-dihydro-dibenzo[b,e]oxepin-11-yl)methylamino]piperidin-1-yl}-1,3,5-triazine, m.p. (cap): 95°-97° C., in accordance with Example 3.

20. 2,4-diallylamino-6-{4-[(5,6,7,12-tetrahydrodibenzo[a,d]cycloocten-12-yl)methylamino]piperidin-1-yl}-1,3,5-triazine, m.p. (cap): 122° C., in accordance with Example 3.

21. 2,4-diallylamino-6-{4-[(8-chloro-10,10-dioxo-11-methyl-(R,S)-dibenzo[c,f]thiazepin-5-yl)methylamino]-piperidin-1-yl}-1,3,5-triazine, m.p. (cap): 153°-155° C., in accordance with Example 3.

22. 2-allylamino-4-ethylamino-6-{4-[(10,11-dihydro-5H-dibenzo[a,d]cyclohepten-5-yl)methylamino]piperidin-1-yl}-1,3,5-triazine, m.p. (cap): 120°-122° C., in accordance with Example 3.

23. 2,4-diallylamino-6-{4-[(10,11-dihydro-5H-dibenzo[a,d]cyclohepten-5-yl)aminomethyl]piperidin-1-yl}-1,3,5-triazine, m.p. (cap): 109°-110° C., in accordance with Example 3.

24. 2,4-diallylamino-6-{4-[(10,11-dihydro-5H-dibenzo[ a,d]cyclohepten-5-yl)methylamino]piperazin-1-yl}-1,3,5-triazine, m.p. (cap) of the corresponding fumarate: 138°-142° C.

25. 2,4-diallylamino-6-{4-[(10,11-dihydro-5H-dibenzo[a,d]cyclohepten-5-yl)methyl]piperazin-1-yl}-1,3,5-triazine, m.p. (cap) 104°-105° C., in accordance with Example 1.

26. 2,4-diallylamino-6-{4-[((R,S)-6,11-dihydro-dibenzo[b,e]thiepin-11-yl)methylamino]piperidin-1-yl}-1,3,5-triazine, m.p. (cap): 131°-132° C., in accordance with Example 3.

27. 2,4-diallylamino-6-{4-[((R,S)-6,11-dihydro-dibenzo[b,e]-6-oxoazepin-11-yl)methylamino]piperidin-1-yl}-1,3,5-triazine, m.p. (cap): 185°-187° C., in accordance with Example 3.

28. 2-allylamino-4-methylamino-6-{4-[((R,S)-6,11-dihydro-dibenzo[b,e]oxepin-11-yl)methylamino]piperidin-1-yl}-1,3,5-triazine, m.p. (cap): 113°-116° C., in accordance with Example 3.

29. 2-allylamino-4-ethylamino-6-{4-[((R,S)-6,11-dihydrodibenzo[b,e]oxepin-11-yl)methylamino]piperidin-1-yl}-1,3,5-triazine, m.p. (cap): 106°-107° C., in accordance with Example 3.

30. 2,4-diallylamino-6-{4-[N-((10,11-dihydro-5H-dibenzo[a,d]cyclohepten-5-yl)methyl)-N-methylamino]piperidin-1-yl}-1,3,5-triazine, m.p. (cap): 105°-107° C., in accordance with Example 3.

31. 2,4-diallylamino-6-{4-[((R,S)-10,11-dihydro-5H-2-methoxydibenzo[a,d]cyclohepten-5-yl)methylamino]-piperidin- 1-yl)-1,3,5-triazine, m.p. (cap) of the corresponding difumarate: 184°-187° C., in accordance with Example 3.

32. 2,4-diallylamino-6-{4-[((R,S)-6,11-dihydro-5,5-dioxo-dibenzo[b,e]thiepin-11-yl)methylamino]piperidin-1-yl}-1,3,5-triazine, m.p. (cap): 116°-119° C., in accordance with Example 3.

The starting materials, other than those mentioned in Examples 1 to 3, are listed in the following Tables.

TABLE A

Compounds of formula II:

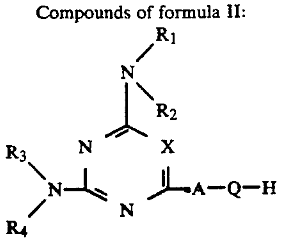

| $R_1$ | $R_2$ | $R_3$ | $R_4$ | X | A | B | M.p. °C. |
|---|---|---|---|---|---|---|---|
| H | allyl | H | propyl | N | — | 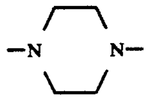 | 100 (K) |
| H | allyl | H | allyl | N | — | 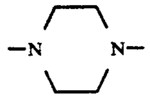 | 259-263 (K) |
| H | allyl | H | allyl | N | — | 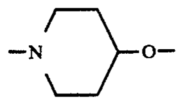 | 118-119 (cap) |
| H | allyl | H | allyl | N | — | 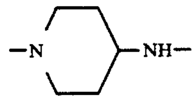 | 218-220 (cap) |

TABLE B

Compounds of formula III:

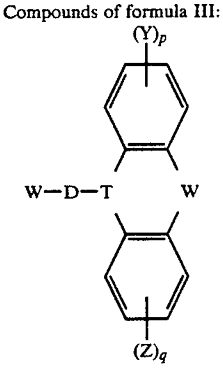

| W | D | T | W | (Y)p | (Z)q | M.p. °C. |
|---|---|---|---|---|---|---|
| Cl | — | CH | $(CH_2)_2$ | H | H | 110 (K) |
| Cl | $-CH_2-$ | CH | — | H | H | 108 (K) |

TABLE C

Compounds of formula IV:

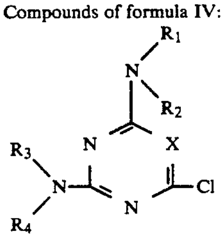

| $R_1$ | $R_2$ | $R_3$ | $R_4$ | X | M.p. °C. |
|---|---|---|---|---|---|
| H | allyl | H | H | N | 161-162 (cap) |
| H | allyl | H | allyl | N | 206-208 (cap) |

TABLE C-continued
Compounds of formula IV:
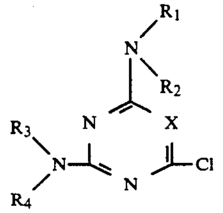
| R1 | R2 | R3 | R4 | X | M.p. °C. |
|---|---|---|---|---|---|
| H | allyl | H | propyl | N | 210 (K) |
| H | allyl | H | allyl | CH | 204 (K) |
TABLE D
Compounds of formula V:
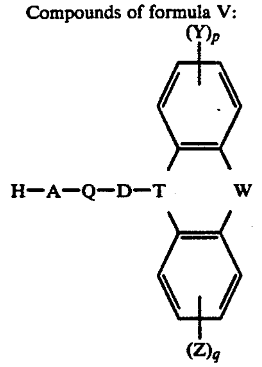
| A | Q | D | T | W | (Y)p | (Z)q | M.p. °C. |
|---|---|---|---|---|---|---|---|
| — | 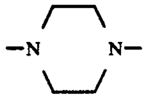 | — | CH | $(CH_2)_2$ | H | H | 99-100 (cap) |
| $HN-(CH_2)_2-$ | 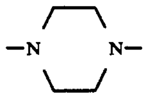 | — | CH | $(CH_2)_2$ | H | H | 70-71 (cap) |
| $HN-CH_2-CH(OH)-CH_2$ | 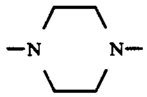 | — | CH | $(CH_2)_2$ | H | H | 100 (cap) |
TABLE E
Compounds of formula VI:
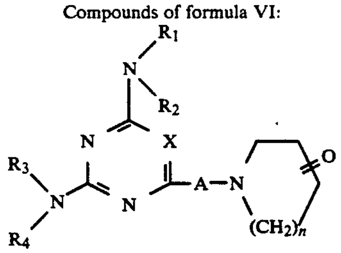
| R1 | R2 | R3 | R4 | X | A | 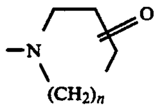 | M.p. °C. |
|---|---|---|---|---|---|---|---|
| H | H | H | H | N | — | 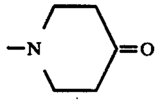 | HCl, 214 (K) |
| $CH_3$ | $CH_3$ | $CH_3$ | $CH_3$ | N | — | 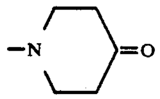 | 2HCl, 144 (K) |

TABLE E-continued
Compounds of formula VI:
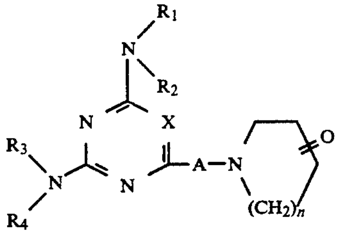
| $R_1$ | $R_2$ | $R_3$ | $R_4$ | X | A | 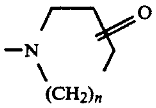 | M.p. °C. |
|---|---|---|---|---|---|---|---|
| H | allyl | H | propyl | N | — | 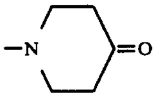 | HCl, 220 (K) |
| H | allyl | H | allyl | N | — | 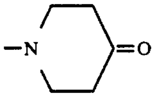 | HCl, 219-222 (cap) |
| H | allyl | H | allyl | N | — | 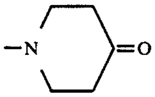 | 232 (K) |
| H | allyl | H | allyl | N | — | 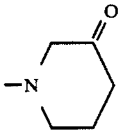 | HCl, 192 (K) |
| H | allyl | H | allyl | N | $-NH-(CH_2)_2-$ | 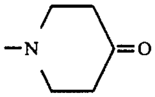 | amorphous |
| H | allyl | H | allyl | N | $-NH-CH(OH)-CH_2-$ | 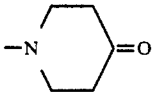 | amorphous |
| H | allyl | H | allyl | CH | — | 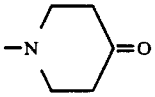 | fumarate, 240 (cap) |

TABLE F

Compounds of formula VII:

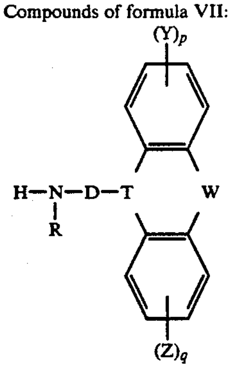

| R | D | T | W | (Y)p | (Z)q | M.p. °C. |
|---|---|---|---|---|---|---|
| H | $CH_2$ | CH | $(CH_2)_2$ | H | H | HCl, 270–280 (cap) |
| H | $CH_2$ | CH | CH=CH | H | H | HCl, 276 (cap) |
| H | $CH_2$ | CH | O | H | H | HCl, 230–235 (cap) |
| H | $CH_2$ | CH | — | H | H | HCl, 272 (cap) |
| H | $CH_2$ | 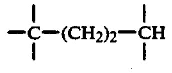 | | H | H | 51–55 (cap) |

EXAMPLE 33

Pharmacological Study

Resistance to anti-cancer agents is a major obstacle to the effectiveness of antitumour drugs. Of the different types of resistance, "Multidrug Resistance" (MDR) is particularly interesting, since it is induced by compounds of natural origin, which are active against solid tumours (anthracyclines, vinca alkaloids, epipodophyllotoxins for example) and is very frequent in certain cancers (colon, for example). When tumour cells are exposed in vitro or in vivo to one of those drugs they become resistant, to varying degrees, to all of those compounds. The resistance phenomenon is as a result of the action of an inducible membrane protein, gP 170, the role of which is to increase the efflux of the cytotoxic agent, thus reducing its intracellular concentration, which results in the loss of sensitivity of those cells to the drug.

Some medicaments, used in other pathologies, are known to reverse that resistance partially or completely (Tsuruo T., Mechanisms of multidrug resistance and implications for therapy. Int. J. Cancer Res., 79, 285–296, 1988; Rothenberg, M and Ling V., Multidrug resistance: molecular biology and clinical relevance, J.N.C.I., 81. 907–910, 1989; Gottesman M. M. and Pastan, I., Resistance to multiple chemotherapeutic agents in human cancer cells, Trends Pharmacol. Sci., 9, 54–58, 1989; Endicott J. A. and Ling V., The biochemistry of P-glycoprotein-mediated multidrug resistance, Annu. Rev. Biochem., 58. 137–171, 1989).

When the modulating agent is added at the same time as the cytotoxic agent, it reduces or completely suppresses MDR-type resistance. Certain medicaments, such as verapamil, amiodarone or cyclosporin, have been used clinically to overcome that resistance, but their intrinsic pharmacological properties and their toxicity limit their use considerably. This gives rise to the interest in searching for compounds that reverse the MDR phenotype but that do not have other pharmacological properties and that are non-toxic.

Moreover, the mechanism of the resistance to chloroquine developed by Plasmodium falciparum is similar. Verapamil restores the sensitivity of a resistant line (Krogstad D. J., Gluzman I. Y., Kule D. E., Oduola A. M. J., Martin S. K., Milhous W. K., Schlessinger P. H., Efflux of Chloroquine from Plasmodium falciparum: mechanism of chloroquine resistance, Science, 238. 1283–1285, 1987; Martin S. K., Oduola A. M. J., Milhous W. K., Reversal of Chloroquine resistance in Plasmodium falciparum by Verapamil, Science, 235, 899–901, 1987), which demonstrates the potential value for use in parasitology of compounds that reverse the MDR phenotype of tumour cells.

The pharmacological study of the compounds of the present invention consisted first of all in an evaluation in vitro carried out on resistant cells. The parameter measured is the cytotoxicity of the antitumour drug, quantified in the absence and in the presence of the reversing compound.

Also measured was the effect of the compounds on the intracellular concentration of the cytotoxic agent. In effect, the known compounds for reversing MDR act by increasing the intracellular concentration of cytotoxic agent. This effect is the consequence of inhibiting the action of gP 170 which is responsible for the efflux of the drug.

This study was completed by an in vivo study, using a murine leukaemia resistant to vincristine (P/388/VCR) and using the compounds in association with vincristine.

MATERIAL AND METHODS

1) Activity in vitro

Cytotoxicity

Two resistant cellular lines were used:

1 Human epidermoid carcinoma, KB-Al, the resistance of which was induced by adriamycin (ADR). Its resistance factor is 200 in relation to the sensitive line (mean resistance).

1 Chinese hamster lung line, DC-3F/AD, the resistance of which was induced by actinomycin D. Its resistance factor is greater than 10,000, and it is thus an extremely resistant line. These two lines are also resistant to vinca alkaloids (vincristine and vinblastine). The cells are cultivated in a complete culture medium (RPMI 1640), containing 10% foetal calf serum, 2 mM glutamine; 50 units/ml penicillin, 50 μg/ml streptomycin, 10 mM Hepes.

The cells are distributed on microplates and exposed to the cytotoxic compounds (actinomycin D for line DC-3F/AD and adriamycin for line KB-Al) at 9 concentrations (2 by 2 series dilutions). The compounds tested for their capacity to reverse MDR are added at the same time as the cytotoxic agent.

The cells are then incubated for 4 days. The number of viable cells is then quantified by a colorimetric assay, the Microculture Tetrazolium Assay (Carmichael J., DeGraff W. G., Gazdar A. F., Minna J. D. and Mitchell J. R. Evaluation of a tetrazolium-based semiautomated colorimetric assay: assessment of chemosensitivity testing, Cancer Res., 47. 936–942, 1987). The results are expressed as $IC_{50}$, the concentration of cytotoxic agent that inhibits the proliferation of the control cells by 50%. The results are expressed as a reversion factor (RF):

$$RF = \frac{IC_{50}\text{ cytotoxic agent only}}{IC_{50}\text{ cytotoxic agent in the presence of the reversing compound}}$$

Flow cytometry

Certain anti-cancer compounds such as adriamycin (ADR) exhibit the property of being fluorescent after excitation by a light source of known wavelength. By measuring that fluorescence, it is thus possible to obtain a relative measurement of the intracellular concentration of ADR. Flow cytometry (FCM) is a preferred method of carrying out this kind of measurement and thus determining quickly if certain active compounds cause an increase in the intracellular concentration of ADR.

The cells $500\times10^3$ per ml were exposed simultaneously to ADR at a fixed concentration (50 $\mu$M) and to the tested compounds at various concentrations. After 5 hours' incubation, the intracellular accumulation of ADR was evaluated by FCM. The analyses were carried out on a flow cytometer ATC3000 (BRUKER-FRANCE) fitted with a 2025 argon laser (SPECTRA-PHISICS-FRANCE) optimised at 488 nm for a capacity of 600 mW. The analysis of each of the samples was carried out on a total of 10,000 cells at a rate of 1,000 cells per second.

The results were presented in the form of linear histograms of the intracellular ADR fluorescence.

Expression of the results: for each of the histograms the mean fluorescence per channel (MEAN) was determined by the information system of the apparatus. For all experiments:

- a negative control (cells without ADR) fixed the autofluorescence threshold.
- a positive control (cells with ADR) determined the MEAN value=MN1.
- the "test" tubes (cells with ADR and with compound) were used to determine, for each of the compounds and at each of the concentrations, the MEAN values=MN2.

The results are expressed in the form of variations from the mean fluorescence obtained for each of the "test" tubes (MN2) in relation to the mean fluorescence obtained with the positive control (MNl): VAR-MEAN=MN2-MN1. The parameter expressed is thus the increase in ADR fluorescence in the presence of the tested compounds.

2) Activity in vivo

Antitumour Activity

The sensitive parent line P 388 (murine leukaemia) and the sub-line resistant to vincristine, P 388/VCR, were supplied by NCI (Frederick, USA). The tumour cells ($10^6$ cells) were inoculated on day 0 into the intraperitoneal cavity of female B6D2Fl mice (Iffa Credo, France) weighing from 18 to 20 g (groups of 8 to 10 animals).

Every day for 4 days, starting from day 1, the animals received:

- an administration by the i.p. route of 50 or 100 mg/kg of the compound of the present invention to be tested, then
- 30 to 60 minutes later, an administration by the i.p. route of 0.25 mg/kg of vincristine (used as a reference antitumour agent).

The tumour activity is expressed as follows:

$$\frac{T}{C}\,\% = \frac{\text{Median survival time of the treated animals}}{\text{Median survival time of the control animals}} \times 100$$

The values are mean values obtained in independent experiments (± sem when n is greater than or equal to 3).

RESULTS

1) Activity in vitro

Cytotoxicity

Table 1 gives the reversion factor values obtained with the various compounds with the line DC-3F/AD and Table 2 with the line KB-A1.

Flow cytometry

Table 3 gives the increase in the ADR fluorescence (VAR-MEAN) obtained with the various compounds with the line DC-3F/AD and Table 4 with the line KB-A1.

2) Activity in vivo

Table 5 shows the increase in an antitumour activity of vincristine in vivo obtained with various representative compounds of the present invention.

All of the tested compounds of the Examples of the invention substantially increase the antitumour activity of vincristine in resistant cells and are, for the most part, more active than verapamil.

TABLE 1

Reversion factors (cytotoxicity) with the line DC-3F/AD

| COMPOUNDS | CONCENTRATIONS 0.5 $\mu$M | 1 $\mu$M | 2.5 $\mu$M | 5 $\mu$M |
|---|---|---|---|---|
| REFERENCE COMPOUND VERAPAMIL | 0.9 | 0.9 | 1.2 | 2.5 |
| COMPOUND OF THE EXAMPLES | | | | |
| 1 | — | 27 | 142 | 309 |
| 2 | 0.8 | 1 | 22 | — |
| 3 | 43 | 236 | 1474 | 3187 |
| 4 | 21 | 66 | 346 | 755 |
| 5 | 3.8 | 81 | 906 | 2753 |
| 6 | 0.9 | 1.1 | 44 | — |
| 7 | 1.2 | 1.1 | 1.6 | 9.7 |
| 8 | 0.8 | 1.6 | 50 | 353 |
| 9 | 4.8 | 39 | 251 | 844 |
| 10 | 1 | 1.9 | 23 | 96 |
| 11 | 2 | 26 | 364 | 1408 |
| 12 | 0.9 | 0.9 | 2.4 | 64 |
| 13 | 2.1 | 7.1 | 36 | 170 |
| 14 | 1.3 | 7.8 | 47 | 187 |
| 15 | 0.8 | 1 | 1.4 | 120 |
| 16 | 1 | 0.9 | 1 | 1.8 |
| 17 | 0.8 | 0.8 | 0.9 | 1.1 |
| 18 | 1.2 | 3 | 64 | 421 |
| 19 | 3.8 | 63 | 549 | 2525 |
| 20 | 3.4 | 52 | 447 | 2951 |
| 21 | 1.2 | 18 | 883 | 2804 |
| 22 | 32 | 177 | 1417 | 2499 |
| 23 | — | 1.4 | 49 | 173 |
| 24 | 2.5 | 14 | 79 | 329 |
| 25 | — | 13 | 127 | 464 |
| 26 | — | 6.8 | 168.9 | 866.6 |
| 27 | — | 1.1 | 1.3 | 2.1 |
| 28 | — | 18.1 | 113.8 | 600.4 |
| 29 | 1.7 | 33.8 | 266.9 | 1327.5 |
| 30 | — | 2.3 | 59.8 | 834.0 |
| 31 | 3.1 | 85.9 | 761.3 | 1913.4 |
| 32 | — | 1.3 | 1.9 | 27.4 |

TABLE 2

Reversion factors (cytotoxicity) with the line KB-A1

| COMPOUNDS | CONCENTRATIONS 0.5 μM | 1 μM | 2.5 μM | 5 μM |
|---|---|---|---|---|
| REFERENCE COMPOUND VERAPAMIL | 1.5 | 5.8 | 23 | 27 |
| COMPOUND OF THE EXAMPLES | | | | |
| 1 | 1.7 | 4 | 16 | 36 |
| 2 | 0.8 | 1.4 | 32 | — |
| 3 | 91 | 131 | 217 | 252 |
| 4 | 42 | 54 | 99 | 142 |
| 5 | 119 | 153 | 258 | 221 |
| 6 | 1.1 | 1.2 | 26 | 18 |
| 7 | 1.8 | 1.7 | 2.3 | 10 |
| 8 | 1.8 | 7.8 | 29 | 12 |
| 9 | 72 | 96 | 163 | 140 |
| 10 | 2.3 | 6.4 | 20 | — |
| 11 | 156 | 228 | 212 | 641 |
| 12 | 1.2 | 3 | 63 | |
| 13 | 16 | 17 | 22 | 57 |
| 14 | 13 | 17 | 20 | 6.9 |
| 15 | 0.8 | 1 | 13 | — |
| 16 | 0.8 | 0.9 | 11 | — |
| 17 | 0.8 | 0.8 | 1.2 | 6.8 |
| 18 | 4.9 | 13 | 49 | 89 |
| 19 | 132 | 153 | 228 | 270 |
| 20 | 35 | 66 | 92 | 177 |
| 21 | 22 | 36 | 93 | 147 |
| 22 | 86 | 116 | 145 | 201 |
| 23 | 18 | 48 | 92 | 126 |
| 24 | 13 | 24 | 41 | 93 |
| 25 | 7.1 | 15 | 28 | 63 |
| 26 | 60.2 | 122.1 | 246.7 | 393.5 |
| 27 | 15.3 | 84.8 | 189.4 | 314.7 |
| 28 | 88.0 | 93.1 | 158.2 | 183.1 |
| 29 | 132.7 | 147.0 | 277.0 | 229.1 |
| 30 | 12.3 | 27.7 | 71.2 | 117.6 |
| 31 | 121.8 | 175.8 | 258.9 | 263.9 |
| 32 | 17.8 | 44.3 | 109.2 | 252.9 |

TABLE 3

Measurement of the intracellular accumulation of adriamycin by cells of the line DC-3F/AD

| COMPOUNDS | VAR-MEAN AT CONCENTRATIONS OF 1.0 μM | 2.5 μM | 5.0 μM | 10 μM |
|---|---|---|---|---|
| REFERENCE COMPOUND VERAPAMIL | 2.1 | 4.0 | 5.6 | 8.9 |
| COMPOUND OF THE EXAMPLES | | | | |
| 1 | 8.4 | 4.9 | 16.0 | 19.3 |
| 2 | 10.1 | 14.7 | 10.2 | 10.5 |
| 3 | 20.2 | 25.8 | 28.3 | 29.6 |
| 4 | 16.2 | 21.8 | 25.5 | 28.1 |
| 5 | 17.9 | 23.5 | 27.3 | 24.9 |
| 6 | 11.0 | 14.4 | 24.3 | 27.6 |
| 7 | 3.4 | 3.9 | 10.1 | 17.4 |
| 8 | 1.3 | 11.4 | 19.3 | 21.0 |
| 9 | 13.4 | 18.1 | 19.4 | 25.7 |
| 10 | 12.3 | 13.5 | 20.2 | 30.7 |
| 11 | 12.7 | 20.2 | 24.5 | 25.8 |
| 12 | 5.4 | 10.3 | 10.4 | 18.3 |
| 13 | 8.1 | 12.0 | 19.6 | 23.2 |
| 14 | 12.3 | 14.5 | 29.4 | 30.6 |
| 15 | 10.1 | 12.4 | 13.7 | 12.4 |
| 16 | 9.9 | 11.8 | 10.4 | 12.9 |
| 17 | 9.4 | 11.0 | 10.5 | 12.6 |
| 18 | 5.5 | 7.4 | 6.7 | 11.0 |
| 19 | 13.1 | 22.6 | 25.5 | 25.3 |
| 20 | 8.2 | 19.7 | 22.3 | 21.6 |
| 21 | 8.1 | 21.1 | 22.8 | 24.1 |
| 22 | 15.1 | 21.9 | 23.1 | 24.9 |
| 23 | 10.0 | 14.6 | 14.0 | 20.5 |
| 24 | 12.8 | 16.9 | 21.1 | 28.2 |
| 25 | 9.9 | 14.7 | 17.6 | 24.5 |
| 26 | 4.3 | 17.8 | 33.5 | 32.6 |

TABLE 3-continued

Measurement of the intracellular accumulation of adriamycin by cells of the line DC-3F/AD

| COMPOUNDS | VAR-MEAN AT CONCENTRATIONS OF 1.0 μM | 2.5 μM | 5.0 μM | 10 μM |
|---|---|---|---|---|
| 27 | 0.0 | 0.0 | 2.2 | — |
| 28 | 4.3 | 12.8 | 16.8 | 21.5 |
| 29 | 6.4 | 13.3 | 18.0 | 21.8 |
| 30 | 5.9 | 12.3 | 17.8 | 19.0 |
| 31 | 9.4 | 26.6 | 30.8 | — |
| 32 | 0.0 | 1.9 | 12.4 | — |

TABLE 4

Measurement of the intracellular accumulation of adriamycin by cells of the line KB-A1

| COMPOUNDS | CONCENTRATIONS 0.5 μM | 1.0 μM | 2.5 μM | 5.0 μM |
|---|---|---|---|---|
| REFERENCE COMPOUND VERAPAMIL | 6.4 | 8.0 | 11.1 | 17.0 |
| COMPOUND OF THE EXAMPLES | | | | |
| 1 | 4.7 | 4.5 | 8.2 | 11.2 |
| 2 | 3.6 | 5.6 | 16.2 | 26.2 |
| 3 | 22.5 | 27.5 | 40.9 | 47.6 |
| 4 | 13.0 | 17.9 | 25.8 | 34.2 |
| 5 | 20.1 | 25.9 | 34.5 | 42.0 |
| 6 | 3.1 | 4.8 | 18.2 | 29.2 |
| 7 | 1.9 | 1.0 | 1.9 | 1.9 |
| 8 | 0.4 | 0.4 | 6.7 | 9.8 |
| 9 | 24.9 | 31.2 | 37.3 | 43.9 |
| 10 | 8.2 | 11.7 | 17.2 | 22.2 |
| 11 | 35.1 | 38.6 | 49.3 | 54.1 |
| 12 | 4.1 | 4.2 | 8.4 | 14.5 |
| 13 | 11.3 | 12.9 | 16.2 | 20.6 |
| 14 | 7.9 | 11.3 | 12.8 | 16.4 |
| 15 | 3.4 | 4.9 | 11.5 | 20.9 |
| 16 | 2.6 | 2.5 | 6.4 | 13.0 |
| 17 | 2.6 | 3.1 | 4.2 | 5.5 |
| 18 | 0.0 | 2.0 | 8.0 | 16.3 |
| 19 | 23.4 | 29.7 | 40.0 | 47.6 |
| 20 | 22.0 | 21.6 | 30.8 | 44.1 |
| 21 | 13.5 | 15.1 | 26.9 | 39.8 |
| 22 | 18.9 | 23.2 | 35.8 | 45.9 |
| 23 | 8.5 | 13.8 | 22.1 | 29.8 |
| 24 | 5.0 | 10.0 | 15.9 | 22.8 |
| 25 | 7.6 | 9.4 | 16.4 | 29.7 |
| 26 | 22.8 | 29.6 | 42.5 | 57.3 |
| 27 | 10.2 | 25.3 | 37.2 | 48.4 |
| 28 | 24.7 | 27.0 | 38.5 | 35.9 |
| 29 | 24.9 | 33.2 | 37.2 | 38.8 |
| 30 | 11.3 | 14.8 | 16.7 | 25.6 |
| 31 | 32.8 | 44.7 | 57.4 | 72.6 |
| 32 | 14.9 | 23.8 | 36.5 | 49.4 |

TABLE 5

Increase in the antitumour activity of vincristine caused by products of the present invention or a reference product (verapamil), on the resistant line P/388/VCR

| TEST COMPOUNDS | DOSE mg/kg i.p. | T/C % |
|---|---|---|
| NO COMPOUND | — | 146 ± 2 |
| REFERENCE COMPOUND VERAPAMIL | 50 | 164 |
| | 75 | 177 |
| COMPOUNDS OF THE EXAMPLES | | |
| 3 | 50 | 208 ± 23 |
| 3 | 100 | 193 ± 3 |
| 5 | 50 | 184 |
| 5 | 100 | 195 |
| 11 | 50 | 156 |
| 11 | 100 | 168 ± 15 |
| 19 | 50 | 167 ± 7 |
| 19 | 100 | 184 ± 7 |
| 20 | 50 | 161 |

TABLE 5-continued

Increase in the antitumour activity of vincristine caused by products of the present invention or a reference product (verapamil), on the resistant line P/388/VCR

| TEST COMPOUNDS | DOSE mg/kg i.p. | T/C % |
|---|---|---|
| 20 | 100 | 174 |
| 21 | 50 | 154 |
| 21 | 100 | 148 |
| 22 | 50 | 159 |
| 22 | 100 | 165 |
| 28 | 50 | 170 |
| 28 | 100 | 171 |
| 29 | 50 | 171 ± 6 |
| 29 | 100 | 185 ± 7 |
| 31 | 50 | 159 |
| 31 | 100 | 177 |

Altogether, the results of this pharmacological study demonstrated the superiority of the compounds of the present invention compared with verapamil which is used as the reference compound.

We claim:

1. A compound selected from the group consisting of:

A) trisubstituted triazines of formula I:

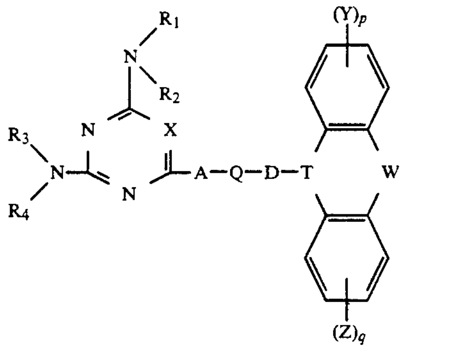

(I)

wherein:

$R_1$, $R_2$, $R_3$ and $R_4$ are the same or different and each represents hydrogen, ($C_1$-$C_6$) cycloalkyl, or straight-chain or branches ($C_1$-$C_6$) alkyl which optionally contains a double or a triple bond;

X represents nitrogen;

A represents a single bond, a straight-chain or branched ($C_1$-$C_3$) hydrocarbon, or —NH—A'— wherein A' represents ($C_2$-$C_6$) hydrocarbon which optionally contains one oxygen or sulphur atom and is optionally substituted by hydroxy;

Q represents:

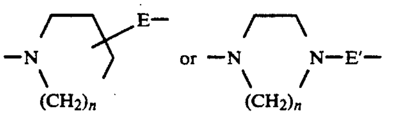

wherein:

n represents an integer of 1 to 3, inclusive,

E represents oxygen or sulphur or —NR— or —$CH_2$NR— wherein R represents hydrogen, ($C_1$-$C_5$) alkyl, or ($C_2$-$C_5$) alkenyl, and E' represents a single bond or —NR— as defined above;

D represents a single bond or straight-chain or branched hydrocarbon up to $C_6$;

T represents:

CR' wherein R' represents hydrogen or ($C_1$-$C_5$) alkyl,

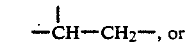

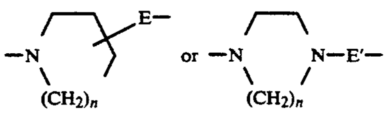

nitrogen;

W represents:

a single bond,

CHR" wherein R" represents hydrogen or ($C_1$-$C_5$) alkyl, $(CH_2)_2$ or $(CH_2)_3$,

—CH═CH—, oxygen or sulphur,

NR"' wherein R"' represents hydrogen or ($C_1$-$C_5$) alkyl,

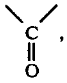 , $SO_2$, —$CH_2$—O—, —$CH_2$—S—, —$CH_2$—$SO_2$—,

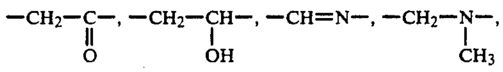

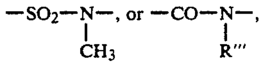

wherein R"' is as defined hereinbefore; and furthermore, when T and W represent CR, and CHR" respectively and R' and R" are other than H, R' and R" may together represent a polymethylene bridge having 2 or 3 carbon atoms;

Y and Z are the same or different and each represents hydrogen, halogen, trifluoromethyl, ($C_1$-$C_3$) alkyl, or alkoxy; and p and q are the same or different and are each 1 or 2;

and, when formula I contains one or more chiral carbons, the corresponding enantiomers or diastereoisomers, and B) the physiologically-tolerable acid addition salts thereof.

2. A compound of claim 1 which is:

2,4-diallylamino-6-{4-[(10,11-dihydro-5H-dibenzo[a,d]cyclohepten-5-yl) methylamino]piperidin-1-yl}-1,3,5-triazine.

3. A compound of claim 1 which is selected from:

2,4-diallylamino-6-[4-(10,11-dihydro-5H-dibenzo[a,d]cyclohepten-5-ylamino)piperidin-1-yl]-1,3,5-triazine and its fumarate.

4. A compound of claim 1 which is selected from:

2,4-diallylamino-6-{4-[(5-H-dibenzo[a,d]cyclohepten-5-yl) methylamino]piperidin-1-yl}-1,3,5-triazine and its difumarate.

5. A compound of claim 1 which is:

2,4-diallylamino-6-{4-[(R,S)-6,11-dihydro-11H-dibenzo [b,e]oxepin-11-yl)methylamino]piperidin-1-yl}-1,3,5-triazine.

6. A compound of claim 1 which is:

2,4-diallylamino-6-{4-[(8-chloro-10,10-dioxo-11-methyl-(R,S)-dibenzo[c,f]thiazepin-5-yl)methylamino]piperidin-1-yl}-1,3,5triazine.

7. A compound of claim 1 which is:

2-allylamino-4-ethylamino-6-{4-[(10,11-dihydro-5H-dibenzo[a,d]cyclohepten-5-yl)methylamino]-piperidin-1-yl}-1,3,5-triazine.

8. A compound of claim 1 which is:

2-allylamino-4-propylamino-6-{4-[(10,11-dihydro-5H-dibenzo[a,d]cyclohepten-5-yl)methylamino]-piperidin-1-yl}-1,3,5-triazine.

9. A pharmaceutical composition comprising as active ingredient an effective resistance-suppressing amount of a compound according to claim 1 together with one or more pharmaceutically acceptable excipients.

10. A method for treating a living animal body having a resistance of tumour cells to anti-cancer agents or a resistance of parasites to anti-parasitic agents, comprising the step of administering to the said living body an amount of a compound of claim 1 which is effective for suppression of the said resistance.

* * * * *

UNITED STATES PATENT AND TRADEMARK OFFICE

CERTIFICATE OF CORRECTION

PATENT NO. : 5,238,936

DATED : August 24, 1993

INVENTOR(S) : Gilbert Regnier, Alain Dhainaut, Ghanem Atassi, Alain Pierre, and Stéphane Leonce It is certified that error appears in the above-indentified patent and that said Letters Patent is hereby corrected as shown below:

Title page, [75]; insert -- , France -- after "Chatenay Malabry", "Chatou", and "Marly le Roi"; insert -- , Belgium -- after "Saint Cloud", and delete "all of" in the last line.

Title page, [30]; insert a decimal point between "91" and "02710".

Col. 2, line 16; "racial" should read -- radical --.

Col. 4, line 55; insert a -- H -- after the "Q".

Col. 6, line 33; "U," should read -- W, --.

Col. 6, line 52; replace the period at the end of the line with a comma.

Col. 7, line 58, "13,8 of" should read --13'8 g of--

Col. 10, line 25; insert -- dihydro-5H- -- between "11-" and "dibenzo[a,d]cy-".

Col. 10, line 53; replace the parenthesis "(" between "6-" and "2-" with a -- { --.

Col. 12, line 13; "B" should read "Q".

Col. 14, lines 1 and 2; these two lines should be below the Formula in Column 13 so that Table C is unbroken.

Col. 17, line 58; replace the period after "58" with a comma.

Col. 18, line 7; replace the period after "238" by a comma.

Col. 18, line 17; "The" should begin a new paragraph.

Col. 19, line 10; "By" should begin a new paragraph.

Col. 20, Table 1; Col. 21, Tables 2 and 3; and Col. 22, Tables 4 and 5; in each place insert a line which goes the width of the Tables between "VERAPAMIL" and "COMPOUND OF".

Col. 22, Table 5; insert a line which goes the width of the Table between "NO COMPOUND - 146±2" and "REFERENCE COMPOUND 50 164".

Col. 24, lines 10-15; delete the two formulas and the word "or".

Col. 24, line 41; "CR," should read -- CR' --.

UNITED STATES PATENT AND TRADEMARK OFFICE

CERTIFICATE OF CORRECTION

PATENT NO. : 5,238,936

DATED : August 24, 1993

INVENTOR(S) : Gilbert Regnier, Alain Dhainaut, Ghanem Atassi, Alain Pierre, and Stephane Leonce It is certified that error appears in the above-indentified patent and that said Letters Patent is hereby corrected as shown below:

Col. 24, line 65, delete the hyphen between "5" and "H".

Signed and Sealed this

Twenty-fourth Day of May, 1994

Attest:

Bruce Lehman

BRUCE LEHMAN

*Attesting Officer*

*Commissioner of Patents and Trademarks*